United States Patent [19]

Duykers et al.

[11] 4,216,766
[45] Aug. 12, 1980

[54] TREATMENT OF BODY TISSUE BY MEANS OF INTERNAL CAVITY RESONANCE

[75] Inventors: Ludwig R. Duykers; Joseph L. Percy, both of San Diego, Calif.

[73] Assignee: The United States of America as represented by the Secretary of the Navy, Washington, D.C.

[21] Appl. No.: 73,399

[22] Filed: Sep. 7, 1979

[51] Int. Cl.³ .............................................. A61B 5/00
[52] U.S. Cl. .................... 128/773; 128/24 A; 128/32
[58] Field of Search ............... 128/24 A, 65, 66, 32, 128/303.1, 2 S

[56] References Cited

U.S. PATENT DOCUMENTS

| | | | |
|---|---|---|---|
| 3,237,623 | 3/1966 | Gordon | 128/24 A |
| 3,338,235 | 8/1967 | Gordon | 128/24 A |
| 3,499,436 | 3/1970 | Balamuth | 128/24 A |
| 3,499,437 | 3/1970 | Balamuth | 128/24 A |
| 3,585,991 | 6/1971 | Balamuth | 128/66 |
| 3,674,018 | 7/1972 | Goldberg | 128/24 A |
| 3,735,756 | 5/1973 | Richards et al. | 128/24 A |
| 3,828,769 | 8/1974 | Mettler | 128/24 A |
| 4,094,306 | 6/1978 | Kossoff | 128/2 V |

Primary Examiner—Lawrence W. Trapp
Attorney, Agent, or Firm—Richard S. Sciascia; Ervin F. Johnston; James O. Skarsten

[57] ABSTRACT

A method and apparatus for treatment of tissue located in a specified region of a mammal, the region being proximate to a gas filled cavity which is contained in a fluid medium within the mammal. The resonance frequency of the cavity is determined, and an acoustic signal having a frequency which is equal to the resonance frequency is directed upon the cavity to resonate the cavity, at a selected level of intensity, until a first phase of treatment has been concluded. Thereupon, a selected second phase in the treatment of the tissue is performed.

15 Claims, 8 Drawing Figures

TREATMENT OF BODY TISSUE BY MEANS OF INTERNAL CAVITY RESONANCE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The invention disclosed and claimed herein pertains generally to a method and apparatus for treating tissue contained within the body of a mammal by vibrating a gas filled cavity, which is proximate to such tissue, at its mechanical resonance frequency. More particularly, the invention pertains to such method and apparatus wherein the cavity is contained in a fluid medium within the mammal, and wherein cavity resonance comprises a first phase of treatment which is to be followed by one or more successive treatment phases.

At present, various techniques are available for the treatment of human or other mammalian body tissue by means of sonic or acoustic waves. Such techniques may be categorized according to the frequency range at which treatment occurs, the frequency range of a technique determining its operating principle. For example, mechanical vibrators, such as massagers and the like, are operated in a range on the order of 60 Hz–120 Hz to couple mechanical vibrations to organic structures by direct contact. Directly coupled vibrations of such frequencies tend to stimulate circulation and relax tense muscles and high strung nerves.

Another class of devices for treating mammalian tissue are those which operate by converting sonic waves into heat at the locations of the treated tissue. Such devices operate in the ultra high sonic frequency range, which is on the order of 800,000 Hz–3,000,000 Hz. The use of such ultra high frequencies in medical therapy for humans is limited by the need to avoid overheating of tissue, to prevent damage thereto.

In a third type of treatment, sonic waves are generated in the low ultrasonic frequency range, which is on the order of 500 Hz–600,000 Hz, to perform micromassage of discrete cells which comprise tissue structure. Such treatment techniques are exemplified by the disclosures of two patents issued to L. Balamuth on Mar. 10, 1970, U.S. Pat. Nos. 3,499,436 and 3,499,437, respectively.

It is to be noted that none of the above techniques employs the vibrations of a gas filled macrocellular cavity, contained within a mammal proximate to tissue to be treated, to accomplish a first phase in therapeutic or other treatment. Yet it is anticipated that by selectively and controllably resonating such a cavity, a number of diverse and very useful tasks may be accomplished which are related to the diagnosis or therapy of various types of health problems. For example, by resonating the lung cavity of a human patient, foreign material such as tar, asbestos or silicone adhering to lung tissue of the patient could be loosened therefrom. The loosened material could then be removed by coughing, or by flushing the lungs with a saline solution, according to a conventionally known procedure. As far as is known, the only other available technique for removing such foreign material is by surgical methods, with their inherent dangers and discomforts.

Lung cavity resonance may also be employed to determine the condition of a patient's lungs or to detect certain health problems. In addition, it has been found that by resonating the lung cavity of an experimental animal at a sufficiently high intensity, lung tissue of the animal may be deliberately damaged in a pattern which very closely resembles the damage which is caused thereto when the animal is afflicted with emphysema. By producing such damage, proposed cures for emphysema may be tested on the animal without the need to actually induce emphysema in it.

SUMMARY OF THE INVENTION

The invention disclosed and claimed herein comprises a method for treatment of tissue located in a specified region of a mammal, the region being proximate to a gas filled cavity which is contained in a fluid medium within the animal, so that the cavity has characteristics of a Helmholtz resonator. The method generally comprises the steps of determining the resonance frequency of the cavity, and directing an acoustic signal upon the cavity to resonate it at a selected level of intensity until a first phase of the treatment has been concluded. Thereafter, a second phase of treatment, which is related to the results of the first phase, is carried out.

In a very useful embodiment of the invention, the determining step comprises the step of determining the resonance frequency of an air filled body cavity of a mammal, the tissue to be treated being contained within the body cavity, and unwanted material adhering to the tissue. The directing step comprises the step of focusing the acoustic signal upon the body cavity until the unwanted material has been loosened from the tissue. The second phase of the treatment comprises the step of passing a selected fluid through the body cavity to wash loosened unwanted material thereoutof.

In another embodiment of the invention, the determining step comprises the step of determining the resonance frequency of a body cavity of a subject mammal, wherein tissue contained within the cavity is susceptible to damage or weakening when a specified health problem occurs in the mammal. The directing step comprises the step of focusing the acoustic signal upon the body cavity until a first set of acoustic data, provided by the body cavity as it is resonating, has been monitored and recorded. The second phase of the treatment comprises the step of comparing the first set of acoustic data with a second set of acoustic data to diagnose the subject mammal for the specified health problem. The second set of acoustic data is provided by resonating the same type of body cavity in a control mammal of the same type as the subject mammal, the control mammal being known to be free of the specified health problem.

In yet another embodiment of the invention, the determining step comprises the step of determining the resonance frequency of a selected macrocellular body cavity of an experimental animal. The directing step comprises the step of focusing the acoustic signal upon the body cavity until a pattern of rupture occurs in tissue of the body cavity which closely resembles damage which would be done to the tissue by a specified health problem, such as emphysema.

Alternatively, the invention comprises apparatus for treating tissue in a specified region of a mammal which is adjacent to a cavity contained within the mammal, the cavity having characteristics of a Helmholtz resonator. The apparatus includes means for generating an acoustic signal having a frequency which is equal to the resonance frequency of the cavity, and also includes means for providing an acoustic channel between the signal generating means and the cavity. Such apparatus further comprises means for directing the acoustic signal through the channel to the cavity to resonate the cavity, at a selected level of intensity, until a first phase of treatment of the tissue has been completed.

OBJECTS OF THE INVENTION

An important object of the present invention is to provide method and apparatus for selectively and controllably resonating an internal cavity of a mammalian subject in order to improve health care and diagnostic techniques for the subject.

Another object is to provide method and apparatus for expelling foreign matter from an internal body cavity of the subject by selectively and controllably resonating the cavity.

Another object is to provide method and apparatus for clearing a blockage of an internal passageway of the subject by resonating a gas filled cavity adjacent to the blockage.

Another object is to provide improved method and apparatus for resonating an internal body cavity of a mammalian subject to test proposed therapeutic techniques for particular health problems.

These and other objects of the invention will become more readily apparent from the ensuing specification when taken together with the drawings.

DESCRIPTION OF THE PREFERRED EMBODIMENT

Figure 1:
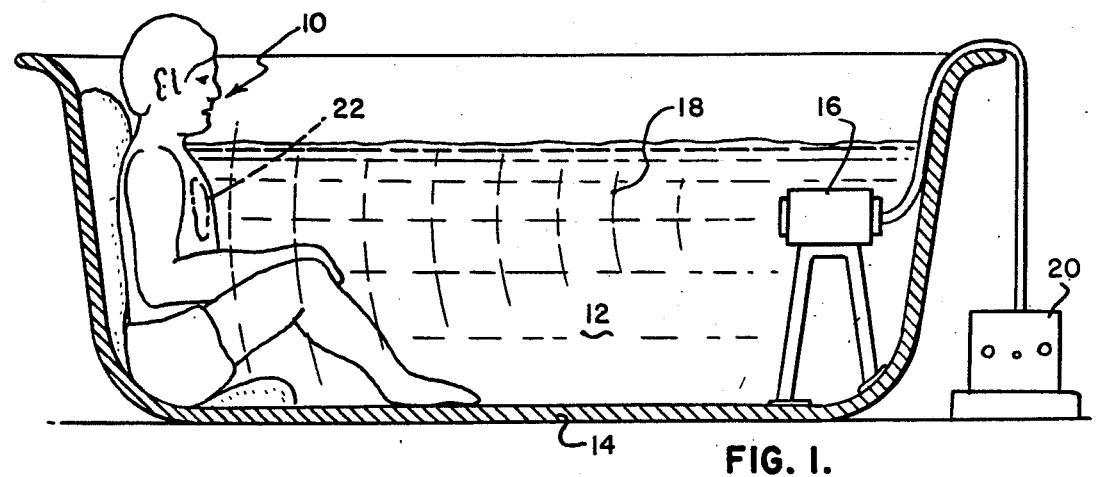
FIG. 1 shows an embodiment of the invention for resonating the lung cavity of a human subject.

Referring to FIG. 1, there is shown a human subject 10 partially submerged in an acoustically conductive medium 12, such as water, contained in a vessel 14. Vessel 14 also contains a transducer 16, which is capable of projecting an acoustic signal 18 into medium 12, the signal having a frequency in the subsonic range, on the order of 1 Hz–100 Hz. The frequency and amplitude of signal 18 is determined by a control device 20 coupled to transducer 16.

Subject 10 is positioned in medium 12 so that his lung cavity 22 is below the surface thereof. Medium 12 provides an acoustic channel between transducer 16 and the submerged portion of subject 10, so that lung cavity 22 is vibrated by signal 18. Since lung cavity 22 of subject 10 is filled with air, has pliant walls, and resides in a fluid filled medium within the body of subject 10, it has the characteristics of a resonator. Consequently, by determining the resonance frequency of lung cavity 22 of subject 10, which is generally on the order of 1 Hz–100 Hz, and then by generating an acoustic signal 18 of such frequency, the tissue of lung cavity 22 may be made to vibrate very vigorously. Foreign matter such as tar, asbestos or silicon which clings to the lung tissue within cavity 22 may thereby be loosened therefrom. At the same time, the amplitude of signal 18 may be kept below a critical threshold to prevent damage to the lung tissue, or to other body parts of subject 10. In previous tests, the lung cavities of human subjects have been resonated by means of a signal 18 having a sound level of 135 db/$\mu$Pa at frequencies of less than 100 Hz.

Figure 2:
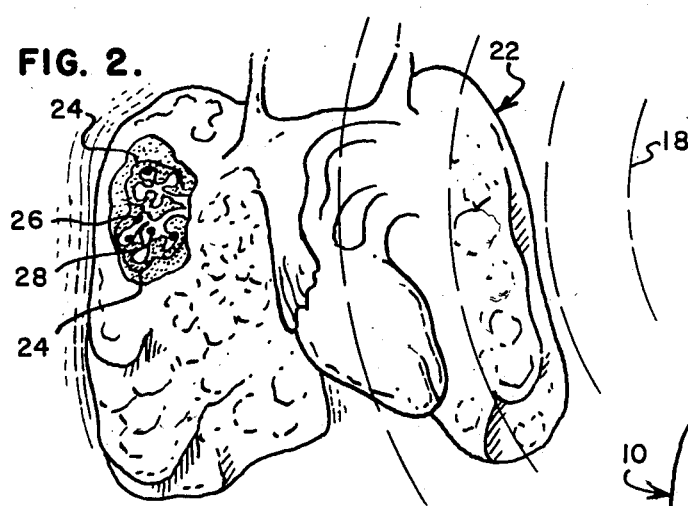
FIG. 2 is a schematic view showing lung tissue of the subject of FIG. 1.

Referring to FIG. 2, there is shown lung tissue 24 of subject 10 which is contained in lung cavity 22, the above type of foreign matter 26 clinging or adhering thereto. FIG. 2 further shows foreign matter 28 which has been shaken loose from lung tissue 24 as lung cavity 22 is vibrated at its resonance frequency by signal 18 for a selected time period, such as 90 seconds. Loosened matter 28 may be expelled from the lungs of subject 10 by coughing, by a conventional vacuuming process, or by flushing the lungs with a saline solution. A conventional technique for such flushing or washing is known as the lavage technique.

Figure 3:
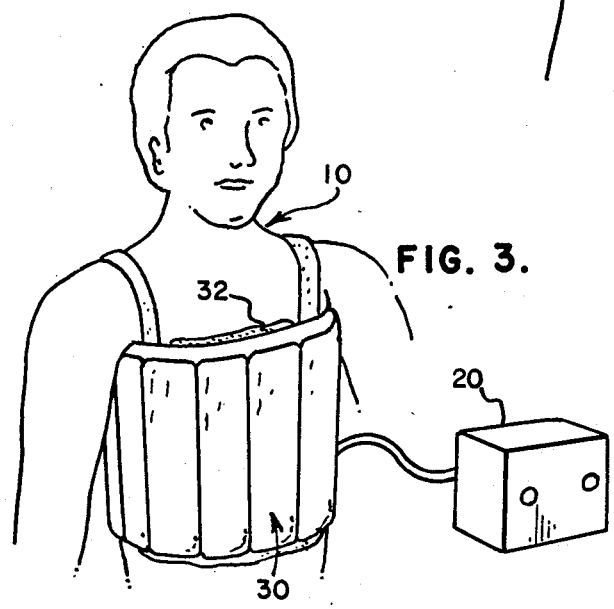
FIG. 3 shows a modification of the embodiment of FIG. 1.

Referring to FIG. 3, there is shown a transducer device 30, known in the art as a cylindrical stacked transducer, surrounding the upper body of subject 10. Stacked transducer 30 is operated by control 20 to generate an acoustic signal 18, which is coupled to lung cavity 22 through an acoustic gel 32 to resonate the lung cavity for a selected period. Acoustic gel 32 comprises an acoustically conductive paste-like material which is positioned between stack transducer 28 and the upper body of subject 10.

Figure 4:
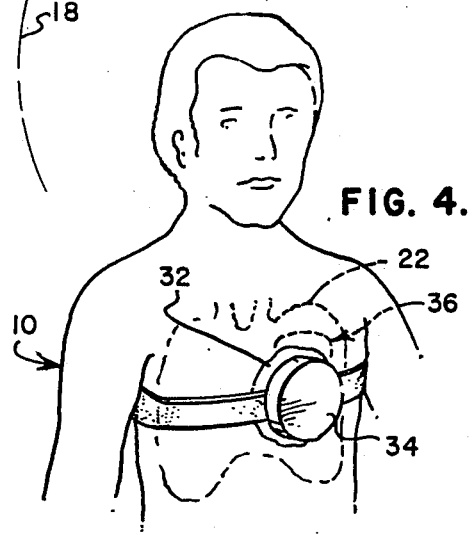
FIG. 4 shows a first embodiment of the invention for resonating a cluster of alveoli of a human lung.

Referring to FIG. 4, there is shown an acoustic transducer 34 which is capable of generating acoustic signals having frequencies in a range on the order of 20 KHz–30 KHz. Transducer 34 is sufficiently small so that if it is strapped to the upper body of subject 10, a signal generated thereby is received by only the lung tissue of subject 10 which is contained within a small region 36 of lung cavity 22.

Figure 5:
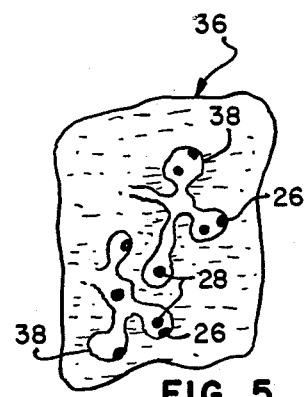
FIG. 5 is a schematic view showing alveoli resonated by the embodiment of FIG. 4.

Referring to FIG. 5, there is shown a cluster of alveoli 38 contained in region 36. Since the diameter of an alveolus is on the order of 250 microns, and since each alveolus 38 comprises an air filled cavity contained in a liquid medium, a signal generated by transducer 34 causes each of the alveoli in region 36 to resonate. Foreign matter 26, adhering to the inner walls of the alveoli, may thereby be shaken loose and expelled.

Figure 6:
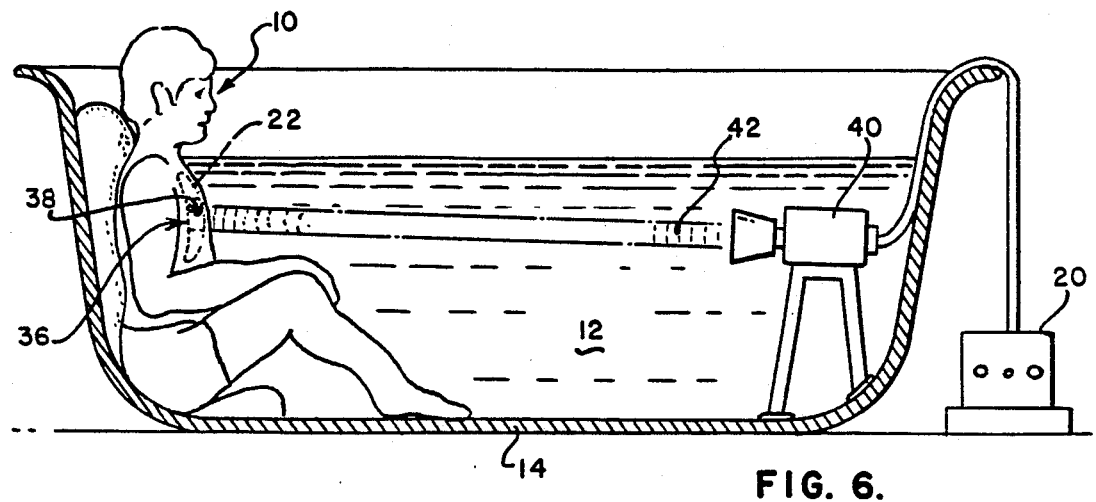
FIG. 6 shows a second embodiment of the invention for resonating a cluster of alveoli of a human lung.

Referring to FIG. 6, there is shown an alternative system for vibrating the individual alveoli 38 which are contained in a region 36 of lung cavity 22. In FIG. 6, subject 10 is once again partially submerged in medium 12, and a transducer 40, capable of generating a signal 42 having a frequency in the range 20 KHz–30 KHz, is also positioned in medium 12. Transducer 40 is a transucer with such precise directivity that signal 42 thereof may be focused on region 36 of lung cavity 22 so that only lung tissue included therein receives signal 42, other lung tissue of subject 10 remaining unaffected thereby. The amplitude and frequency of signal 42 are controlled by control device 20, coupled to transducer 40.

Figure 7:
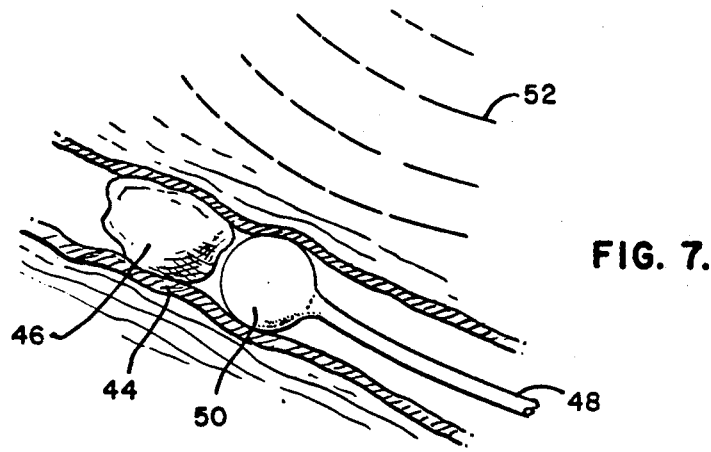
FIG. 7 shows an embodiment of the invention for clearing a blockage from an internal passage of a mammalian subject.

Referring to FIG. 7, there is shown a passage in the body of subject 10, such as a blood vessel 44, which contains a blockage, such as a blood clot 46. To eliminate the blockage, a catheter 48 is inserted into blood vessel 44 so that a minute gas filled balloon 50, joined to the end of catheter 48, is positioned in adjacent relationship with blockage 46. Thereupon, transducer 40 generates a signal 52 which is equal to the resonance frequency of the balloon, signal 52 being focused so that it is received by balloon 50. Balloon 50 is thereby caused to vibrate vigorously to disperse blockage 46.

Figure 8:
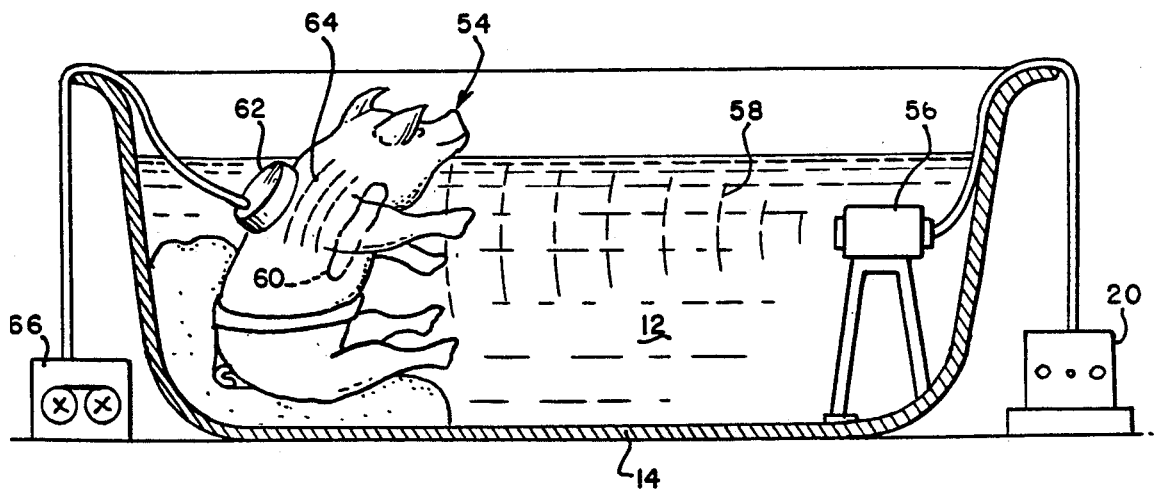
FIG. 8 shows an embodiment of the invention for selectively treating lung tissue of an animal subject.

Referring to FIG. 8, there is shown an animal, such as a swine 54, partially submerged in medium 12. Transducer 56 is also contained in medium 12 for projecting a signal 58 therethrough to resonate lung cavity 60 of swine 54, the resonance frequency of cavity 60 being on the order of 70 Hz. A hydrophone 62 is positioned in relation to swine 54 so that it receives signal 64, signal 64 being an acoustic signal which is generated by resonation of body cavity 60. Hydrophone 62 is further positioned so that swine 54 is between transducer 56 and hydrophone 62 to prevent reflections of projected signal 58 from being detected by hydrophone 62. A standard device 66 is coupled to hydrophone 62 to provide a readout and/or recording of signal 64. Device 66 further comprises a device which is capable of comparing signal 64 with previously recorded acoustic resonations of the lungs of swine which are known to be in sound condition. By making such comparison, the health of animal 54, and in particular, the strength of the lungs thereof, may be readily determined.

Referring further to FIG. 8, it has been found that by operating transducer 56 to generate an acoustic signal of around 65 KHz, the resonance frequency of alveoli of the lungs of swine 54, and by providing such signal with an overall source level which is in excess of 232 db/$\mu$Pa, damage occurs to lung tissue of swine 54 which closely resembles the damage done thereto when the animal has emphysema. Consequently, the system of FIG. 8 may be employed to deliberately produce symptoms of emphysema in lung tissue of swine 54. Swine 54 may then be subjected to a proposed treatment for emphysema, without the need to actually induce emphysema in it.

Obviously, many modifications and variations of the present invention are possible in the light of the above teachings, and, it is therefore understood that within the scope of the disclosed inventive concept, the invention may be practiced otherwise than as specifically described.

What is claimed is:

1. A method for treatment of tissue located in a specified region of a mammal, said region being proximate to a gas filled cavity which is contained in a fluid medium within the mammal, said method comprising the steps of:
   determining the resonance frequency of said cavity;
   generating an acoustic signal having a frequency which is equal to said resonance frequency;
   directing said acoustic signal upon said cavity to resonate said cavity at a selected level of intensity until a first phase of said treatment has been concluded; and
   performing a second phase of said treatment after the conclusion of said first phase.

2. The method of claim 1 wherein:
   said generating step includes the step of generating a signal having an amplitude which is below a critical threshold to prevent said acoustic signal from damaging tissue in said region during said directing step;
   said directing step includes the step of providing an acoustic channel for conducting said acoustic signal from an acoustic transducer to said cavity; and
   said directing step further includes the step of preventing said acoustic signal from impinging upon tissue of said mammal which is not included in said specified region for the duration of said directing step.

3. The method of claim 1 wherein:
   said determining step comprises the step of determining the resonance frequency of an air filled body cavity of a mammal, said tissue to be treated being contained within said body cavity, unwanted material adhering to said tissue to be treated;
   said directing step comprises the step of focusing said acoustic signal upon said body cavity until said unwanted material has been loosened from said tissue; and
   said second phase of said treatment comprises the step of passing a selected fluid through said body cavity to remove said unwanted material from said body cavity.

4. The method of claim 3 wherein:
   said generating step comprises the step of generating an acoustic signal which is in the subsonic frequency range;
   said directing step comprises the step of focusing said acoustic signal upon a human lung until foreign matter adhering to the tissue of said lung has been loosened; and
   said second phase of said treatment comprises the step of flushing said lung with saline solution to expel said loosened foreign material from said lung.

5. The method of claim 3 wherein:
   said generating step comprises the step of generating an acoustic signal which is in a frequency range on the order of 20 KHz–30 KHz;
   said directing step comprises the step of precisely focusing said acoustic signal upon a small number of closely grouped alveoli within a human lung until foreign matter adhering to tissue of said alveoli has been loosened; and
   said second phase of said treatment comprises the step of flushing said lung with saline solution to wash said loosened foreign material away from said alveoli.

6. The method of claim 1 wherein:
   said determining step comprises the step of determining the resonance frequency of a body cavity of a subject mammal which contains tissue which is to be treated, said tissue being susceptible to damage when a specified health problem occurs in said subject mammal;
   said directing step comprises the step of focusing said acoustic signal upon said body cavity until a first set of acoustic data, provided by said body cavity as said body cavity is resonating, has been monitored and recorded; and
   said second phase of said treatment comprises the step of comparing said first set of acoustic data with a second set of acoustic data to diagnose said subject mammal for said specified health problem, said second set of acoustic data being provided by resonating the same type of body cavity in a control mammal of the same type as said subject mammal, said control mammal being known to be free of said specified health problem.

7. The method of claim 1 wherein:

said generating step comprises the step of generating an acoustic signal which is in the subsonic frequency range; and said directing step comprises the step of focusing said acoustic signal on the lung cavity of a subject mammal to resonate said lung cavity until a first set of data has been monitored and recorded which represents the physical condition of the lung tissue of said subject mammal.

8. The method of claim 1 wherein:

said determining step comprises the step of determining the resonance frequency of a selected macrocellular body cavity of an experimental animal; and said directing step comprises the step of focusing said acoustic signal upon said body cavity to resonate said body cavity at a selected level of intensity until a pattern of rupture occurs in tissue of said body cavity which closely resembles the rupture pattern of said tissue which occurs when said experimental animal has a specified health problem.

9. The method of claim 8 wherein:

said directing step comprises the step of focusing said acoustic signal upon the lung cavity of said experimental animal to resonate said lung until rupture occurs in lung tissue of said experimental animal which closely resembles a symptom of emphysema.

10. The method of claim 1 wherein:

said determining step comprises the step of determining the resonance frequency of a minute gas filled balloon which has been inserted into an internal passageway of said mammal, adjacent to a blockage of said passageway; and said directing step comprises the step of precisely focusing said acoustic signal upon said balloon until vibrations generated by said resonating balloon have dispersed said blockage.

11. The method of claim 1 wherein:

said determining step comprises the step of determining the resonance of a minute gas filled balloon joined to a catheter, said balloon and said catheter being inserted into a blood vessel of said mammal so that said balloon is adjacent to a blood clot in said blood vessel; and said directing step comprises the step of precisely focusing said acoustic signal upon said balloon until vibrations generated by said resonating balloon have dispersed said blood clot.

12. Apparatus for expelling foreign matter from a specified body cavity of a mammal, said foreign matter initially adhering to tissue contained within said cavity, said cavity having characteristics of a resonator, said apparatus comprising:

means for generating an acoustic signal, the frequency of said acoustic signal being equal to the frequency at which said cavity resonates;

means for providing an acoustic channel between said signal generating means and said cavity;

focusing means for directing said acoustic signal through said acoustic channel to said cavity to resonate said cavity until said foreign matter has been loosened from said tissue; and means for expelling said loosened foreign matter from said body cavity.

13. The apparatus of claim 12 wherein:

said generating means comprises means for generating an acoustic signal in the subsonic frequency range;

said focusing means comprises means for directing said acoustic signal upon a human lung cavity to resonate said cavity until foreign matter contained within said cavity has been loosened from tissue of said human; and said expelling means comprises means for passing a selected fluid through said lung cavity to remove said loosened foreign material.

14. The apparatus of claim 12 wherein:

said generating means comprises means for generating an acoustic signal having a frequency in a range which is on the order of 20 KHz–30 KHz;

said focusing means comprises means for directing said acoustic signal upon a small region of a human lung to resonate alveoli which is contained in said region until foreign matter contained within said alveoli has been loosened from tissue of said alveoli; and said expelling means comprises means for passing a selected fluid through said alveoli to remove said loosened foreign material.

15. Diagnostic apparatus comprising:

means for generating an acoustic signal, the frequency of said acoustic signal being equal to the frequency at which resonance occurs in a selected gas filled body cavity of a subject mammal;

means for providing an acoustic channel between said signal generating means and said cavity;

focusing means for directing said acoustic signal through said channel to said cavity to resonate said cavity for a selected time period and at a selected level of intensity;

means for monitoring signals generated by the resonation of said cavity during said time period to provide a first set of acoustic data; and means for comparing said first set of acoustic data with a second set of acoustic data to determine the physical condition of said selected body cavity, said second set of acoustic data being obtained by resonating a body cavity of the same type as said selected body cavity, of a control mammal of the same type as said subject mammal which is known to be in sound physical condition.

* * * * *